(12) United States Patent
Macek et al.

(10) Patent No.: US 6,495,710 B2
(45) Date of Patent: Dec. 17, 2002

(54) SYNTHESIS AND USE OF DIMETHYL 1,5-NAPHTHALENEDICARBOXLYATES AND INTERMEDIATES THEREFROM

(75) Inventors: John A. Macek, Naperville, IL (US); Bruce I. Rosen, Morton Grove, IL (US); Juergen K. Holzhauer, Naperville, IL (US); John S. Bramlet, Lockport, IL (US); Larry D. Lillwitz, Yorkville, IL (US); David J. Schneider, Carol Stream, IL (US); Lawrence L. Lang, Aurora, IL (US); Edward E. Paschke, Wheaton, IL (US); John M. Weis, Naperville, IL (US); Yenamandra Viswanath, Naperville, IL (US); Stefanos L. Sakellarides, Naperville, IL (US)

(73) Assignee: BP Corporation North America Inc., Chicago, IL (US)

( * ) Notice: Subject to any disclaimer, the term of this patent is extended or adjusted under 35 U.S.C. 154(b) by 93 days.

(21) Appl. No.: 09/760,415

(22) Filed: Jan. 12, 2001

(65) Prior Publication Data

US 2001/0031852 A1 Oct. 18, 2001

Related U.S. Application Data

(60) Provisional application No. 60/176,145, filed on Jan. 14, 2000.

(51) Int. Cl.$^7$ ............................................. C07C 69/76
(52) U.S. Cl. .............................. 560/100; 560/5; 560/8; 560/18; 560/77; 560/98; 528/298; 528/302; 528/308
(58) Field of Search ........................... 560/5, 8, 18, 77, 560/98, 100; 528/298, 302, 308; 585/410, 411

(56) References Cited

U.S. PATENT DOCUMENTS

| | | | | |
|---|---|---|---|---|
| 4,950,825 A | * | 8/1990 | Sikkenga et al. | 585/320 |
| 4,990,717 A | * | 2/1991 | Sikkeenga | 585/429 |
| 5,030,781 A | * | 7/1991 | Sikkenga et al. | 585/320 |
| 5,034,561 A | * | 7/1991 | Sikkenga et al. | 585/410 |
| 5,073,670 A | * | 12/1991 | Sikkenga et al. | 585/320 |
| 5,198,594 A | * | 3/1993 | Lillwitz et al. | 585/452 |
| 5,284,987 A | * | 2/1994 | Sikkenga et al. | 203/34 |
| 5,334,796 A | * | 8/1994 | Lillwitz et al. | 585/452 |
| 5,401,892 A | * | 3/1995 | Sikkenga et al. | 585/320 |
| 6,252,037 B1 | * | 6/2001 | Kojima et al. | 525/444 |

* cited by examiner

*Primary Examiner*—Samuel A. Acquah
(74) *Attorney, Agent, or Firm*—Scott P. McDonald; Nirav Patel

(57) ABSTRACT

The synthesis of dimethyl-1,5-naphthalenedicarboxylate and polymers and articles formed therefrom is disclosed, as well as applications for dimethyl-1,5-naphthalenedicarboxylate, its corresponding acid 1,5-NDA, and various synthesis intermediates.

9 Claims, 2 Drawing Sheets

US 6,495,710 B2

SYNTHESIS AND USE OF DIMETHYL 1,5-NAPHTHALENEDICARBOXLYATES AND INTERMEDIATES THEREFROM

This application claims the benefit of U.S. provisional patent application Serial No. 60/176,145, filed Jan. 14, 2000.

FIELD OF THE INVENTION

The invention generally relates to the synthesis of naphthalenic compounds, and more particularly relates to the synthesis of 1,5 dimethylnaphthalenes and the use of these compounds and their synthesis intermediates.

BACKGROUND OF THE INVENTION

Polymers based on dimethyl-2,6-naphthalenedicarboxylate (2,6-NDC) are known to be useful in a wide variety of commercial applications.

Films made from 2,6-NDC-based polymers exhibit strength and thermal properties which are superior to films and fibers made from other polymers such as polyethyleneterephthalate (PET). These enhanced properties have led to the use of 2,6-NDC-based polymers in camera films and magnetic recording tapes as well as electrical and electronic components.

2,6-NDC-based polymers also exhibit high resistance to the diffusion of gases such as carbon dioxide, water vapor and oxygen. This resistance to gas diffusion makes these polymers useful in films and containers for a wide variety of food and beverage packaging applications.

The superior physical strength of 2,6-NDC-based polymers also renders these polymers useful in physically demanding applications such as cords for automobile and motorcycle tires.

Unfortunately, the commercial scale synthesis of 2,6-NDC is a complex, multi-step process, which can result in a relatively high price per pound for 2,6-NDC when compared to other polymers.

The synthesis of 2,6-NDC typically includes several steps. In a typical synthesis, orthoxylene and butadiene are reacted over an alkali metal or other catalyst to yield a 5-orthotolylpentene (5-OTP) alkenylation product. The 5-OTP is then cyclized over an acid catalyst to yield 1,5 dimethyltetralin (1,5-DMT). The 1,5 DMT is dehydrogenated over a noble metal or some other dehydrogenation catalyst to yield 1,5-dimethylnaphthalene(1,5-DMN), which is subsequently isomerized to produce 2,6-dimethylnaphthalene (2,6-DMN).

Once 2,6-DMN has been produced, it is oxidized to produce 2,6-naphthalene dicarboxylic acid (2,6-NDA), which is subsequently esterified to produce 2,6-NDC. This 2,6-NDC can then be polymerized in the presence of, for example, ethylene glycol, to produce polyethylenenaphthate (PEN) useful as a monomer or comonomer in applications such as those discussed above.

The foregoing seven step process to produce PEN demands that every synthesis step be selective and produce high yields of the desired end product if NDC is to be manufactured in a commercially economically successful manner.

What is needed is a naphthalenic monomer that can be produced more efficiently and at low cost.

SUMMARY OF THE INVENTION

We find that the economic viability of naphthalenic monomers can be increased in many applications by producing a 1,5-NDC-based material rather than a 2,6-NDC-based material. Elimination of the isomerization reaction and 2,6-DMN purification required to convert 1,5-DMN to 2,6-DMN reduces process cost, increases yield and can increase plant capacity where the isomerization reaction or purification of the isomerized product is a production limiting step. By identifying uses for several intermediates in the 1,5-NDC synthesis reaction, we find that the production of these intermediates need not be carried out in the specific proportion required to manufacture the 1,5-NDC end product material, thereby making the sizing of equipment less critical, and increasing the economic viability of an NDC polymer plant as overproduction of intermediates can be accommodated by diverting excess material to other end uses.

Additionally, we believe that the unique physical and chemical properties of 1,5-NDC make 1,5-NDC a preferred material over other monomers such as isophthalic acid in many applications, thereby increasing demand for NDC materials generally.

DETAILED DESCRIPTION OF THE PREFERRED EMBODIMENTS

Figure 1:
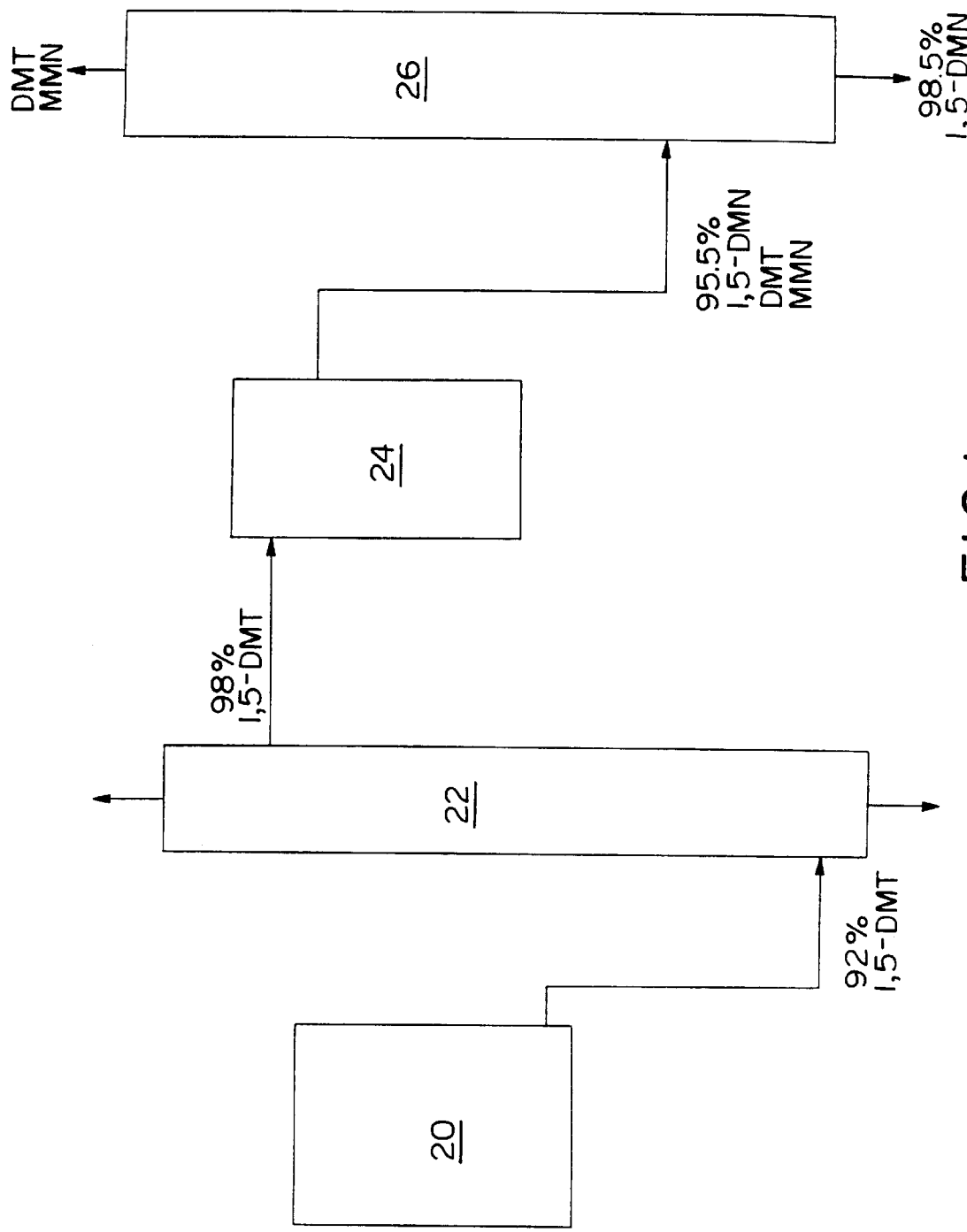
FIG. 1 is a process flow diagram of a process for making 1,5-DMN from 1,5-DMT.

The following description of the synthesis of 1,5-NDC, and the discussion of its end uses and those of its intermediates, is illustrative only. Other embodiments of the invention will be apparent to those skilled in the art after reviewing the following descriptions. The descriptions, therefore, are not intended in any way to limit the scope of our invention.

Synthesis of 1,5-NDC can be performed generally in accordance with the synthesis of 2,6-NDC, except that there is no need to isomerize 1,5-DMN to 2,6-DMN. Elimination of this process step reduces capital and operating costs, in addition to producing a product that may be superior in many applications.

Typically, the first synthesis step in manufacturing 1,5-DMN will be the reaction of orthoxylene and butadiene to yield a 5-orthotolyl pentene (5-OTP) alkenylation product. Examples of alternative methods for alkynelating alkyl benzenes useful in this synthesis step can be found in our U.S. Pat. No. 4,990,717 to Sikkenga; and U.S. Pat. Nos. 5,198,594 and 5,334,796 to Lillwitz et al., the disclosures of which are hereby incorporated by reference.

A preferred method of performing this reaction is to use 10 to 300 ppm of NaK catalyst (a eutectic mixture of Na and K) in the presence of a stoichiometric excess of orthoxylene to butadiene of at least 5:1, at temperatures of between about 80° C. to 150° C., at between 1 and 3 atmospheres of pressure, at residence times of about one hour. Selectivity to 5-OTP can be increased by adding an amine promoter such as N,N,N',N'-tetramethyl ethylene diamine. The reaction preferably is quenched by addition of water, methanol, or a mixture thereof, followed by separation of 5-OTP by any convenient means known in the art.

Cyclization reactions useful for preparing dimethyltetralin intermediates in the synthesis of 1,5-NDC are well-known and typically will involve reacting the 5-OTP intermediate over an acid catalyst. Because a high degree of selectivity is preferred, processes using highly selective Y-type crystalline aluminosilicates of the types disclosed in our U.S. Pat. Nos. 4,950,825; 5,030,781; 5,034,561; 5,073,670; and 5,401,892 to Sikkenga, et al. are preferred. Examples of preparation of dimethyl tetralin in a distillation reactor can be found in our U.S. Pat. No. 5,284,987, also to Sikkenga, et al. The disclosures of the foregoing patents are hereby incorporated by reference.

The reaction preferably will be conducted at an elevated temperature between about 150° C. and 250° C., at pressures between about 0.3 and 5 atmospheres, preferably in the absence of a solvent, although paraffinic or aromatic solvents that are chemically inert under the reaction conditions, such as tetradecane or anthracene, can be used. Water should be excluded from the reaction mixture.

Dehydrogenation of 1,5-DMT can be accomplished, for example, by using any solid dehydrogenation catalyst having a commercially serviceable lifetime under the dehydrogenation conditions employed. Typically, the catalyst will be a noble metal on an active carbon or alumina support, and contain up to about 15 weight percent noble metal based on the total weight of the catalyst. Process conditions suitable for carrying out the dehydrogenation reaction with these and other catalysts can be found in our U.S. Pat. Nos. 5,012,024 and 5,118,892 to Sikkenga, et al., and additional information concerning suitable catalysts for this reaction can be found in our U.S. Pat. Nos. 5,189,234 and 5,401,705 to Amelese, the disclosures of which are hereby incorporated by reference. Typical temperature and pressure process conditions will be approximately the same as those described above for the cyclization reaction.

1,5-NDA typically will be produced by the liquid phase oxidation of 1,5-DMN in the presence of a source of molecular oxygen, a solvent comprising a monocarboxylic acid and water, and a catalyst comprising cobalt, manganese and bromine components, at reaction temperatures of from about 100 to 260° C. The ratios of catalyst components and solvent to feedstock can be determined empirically at the selected reaction temperature and pressure conditions to minimize the formation of undesired reaction products and presence of residual catalyst metals in the 1,5-NDA product. The reaction preferably is performed in a monocarboxylic acid solvent such as acetic acid, or a mixture of acetic acid and water, with a ratio of solvent to DMN of about 2:1 to 12:1, a manganese to cobalt ratio of about 5:1 to 0.3:1, a bromine to manganese plus cobalt ratio of about 0.3:1 to 0.8:1, and a total amount of cobalt plus manganese of up to one weight percent of the selected solvent.

Additional information concerning the oxidation of DMN's to NDA's can be found in our U.S. Pat. No. 5,292,934 to Sikkenga et al. and U.S. Pat. No. 5,254,719 to Holzhauer, et al., the disclosures of which are incorporated by reference. Techniques described in these patents as useful for the oxidation of 2,6 DMN will be easily adapted for the oxidation of 1,5-DMN's by those skilled in the art.

1,5-NDA produced in the foregoing manner may be purified by one or more purification steps prior to esterification to 1,5-NDC to improve the purity and yield of the final NDC product. Suitable methods of purification include recrystallization, solvent washing and/or distillation of the 1,5-NDA oxidation product as will be apparent to those skilled in the art.

Esterification of 1,5-NDA to 1,5-NDC typically will be accomplished by heating a mixture of methanol and 1,5-NDA to a temperature between about 80 and 200° C., at pressures up to about 40 atmospheres, and at residence times on the order of 20 to 150 minutes. Preferred temperature and pressure conditions will be between about 90 and 150° C. and 3 to 15 atmospheres absolute pressure. Temperature and pressure should be selected so that a portion of the methanol is maintained in the liquid state while performing this esterification reaction.

As with the NDA feedstock, purification of the esterification product prior to use as a monomer is preferred, and such purification typically can be accomplished by solvent washing, recrystallization and/or vacuum distillation of the reaction mixture.

Various combinations of the foregoing steps can be used to optimize the purity and yield of 1,5-NDC and its intermediates.

For example, we have produced relatively pure 1,5-DMN by dehydrogenating 1,5-DMT over a platinum on aluminum oxide support to produce 1,5-DMN having a purity of about 88 weight percent. While this 1,5-DMN can be increased to relatively high purity by solvent crystallization, this process is relatively expensive, and distillative purification is not particularly effective due to the relatively close boiling points of 1,5-DMN and the other impurities present in the dehydrogenation reaction product.

FIG. 1 illustrates an alternative process which can be used to economically produce high purity 1,5-DMN from 1,5-DMT. In this process, 92 weight percent pure 1,5-DMT from cyclization reactor 20 was distilled in distillation column 22. Column 22 employed approximately 20 Oldershaw trays, a reflux ratio of about 15 to 1, and a distillation pot temperature of about 253° C. Because the impurities present were mostly relatively lighter boiling OTP's and relatively heavier boiling DMN's, the distillate from column 22 was 98 to 98.5 weight percent 1,5-DMT. This distillate was then dehydrogenated in dehydrogenation reactor 24 over a highly selective dehydrogenation catalyst, which in this case was about 0.5% K and 0.5% Pt on zinc aluminate spinel ($ZnAl_2O_4$), to produce a reaction product containing about 95.5 weight percent 1,5-DMN along with various DMT and monomethylnaphthalate (MMN) impurities. This product was then distilled in a second distillation column 26 to produce 98.5 weight percent pure 1,5-DMN.

Figure 2A:
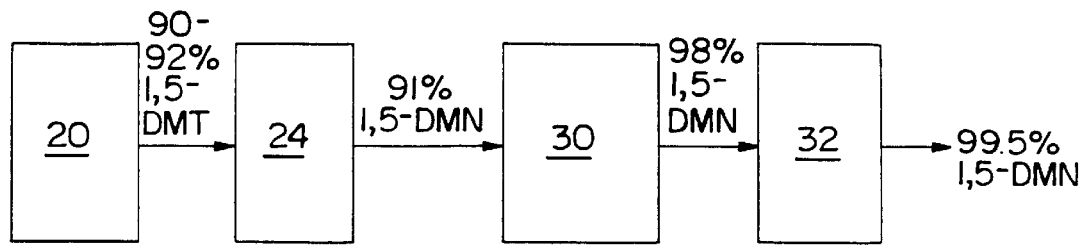
FIGS. 2a and 2b are process flow diagrams illustrating alternative processes for making high purity 1,5-DMN from 5-OTP.
Figure 2B:
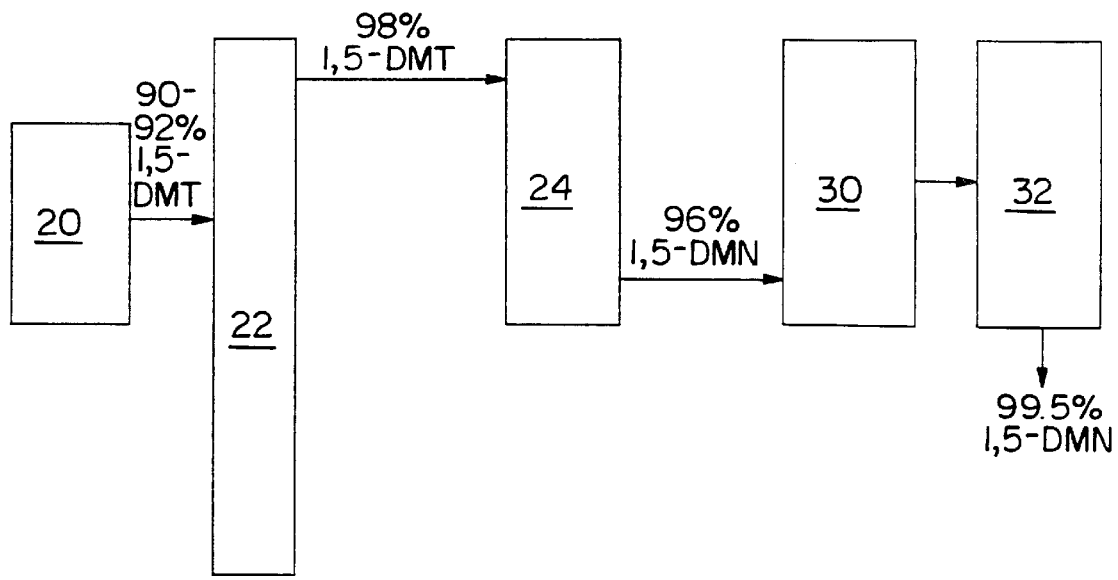

FIGS. 2a and 2b are process flow diagrams illustrating processes for converting 5-OTP to high purity 1,5-DMN.

In FIG. 2a, 5-OTP is cyclized in reactor 20, dehydrogenated in reactor 24, and the resulting 1,5-DMN crystallized in crystallizer 30. To obtain relatively pure (98%), 1,5-DMN from crystallizer 30, crystallizer conditions are selected in which the melt of 1,5-DMN feed is added to crystallizer 30 at a temperature of about 120° C. The rate of addition to crystallizer 30 should be such that the NORPAR solvent (a mixed $C_{10-13}$ solvent available from Exxon Chemical) or other suitable solvent can be maintained at a temperature preferably no greater than about 27° C. Maintaining this temperature differential between the crystal melt and solvent is preferred so that the substantial increase in purity of 1,5-DMN from about 91 to 98% can be accomplished in crystallizer 30. The resulting 98% pure 1,5-DMN product can then be washed in additional NORPAR or other solvent in solvent wash 32 to increase the 1,5-DMN purity to about 99.5%. Other melt and recrystallization solvent temperatures may be used in the foregoing recrystallization step, but it is preferred that the recrystallization solvent be maintained at a temperature at least 60° C. less than the temperature of the melt during the recrystallization step, and more preferably, at least 80° C. less than the temperature of the melt during the recrystallization step.

FIG. 2b differs from FIG. 2a in that distillation tower 22 follows cyclization reactor 20. This increases the purity of 1,5-DMN to dehydrogenation reactor 24 to about 98%. The 1,5-DMN produced in dehydrogenation reactor 24 is approximately 96% pure. Use of crystallizer 30 followed by solvent wash 32 as discussed in connection with FIG. 2b yields 1,5-DMN at purities up to about 99.9%. Use of tower 22 to produce higher quality 1,5-DMT dehydrogenation feed is believed to increase the yield of the purification process by about 10 to 15% when compared to the process of FIG. 2a.

We also have produced purified 1,5-NDC from the crude reaction oxidation product of 1,5-DMN by a process in which we convert the crude acid into an ester via a catalyzed low temperature/pressure esterification in methanol, followed by crystallization in methanol, then followed by distillation of the crystallized product as in Example 1, below.

EXAMPLE 1

1,180 grams of crude 1,5-NDA were charged to a 5 gallon stainless steel reactor along with 10,315 grams of reagent grade methanol, 105 grams of concentrated sulfuric acid and 23.6 grams of water. The reactor was closed and pressurized with nitrogen to 100 psig. This nitrogen purge was repeated 3 times, and the vessel was then heated to reach an internal set point of 120° C. During heat up, the reactor was vented at approximately 55° C. to release dimethyl ether produced by the acid catalyzed reaction of methanol.

When the 120° C. set point temperature was reached, a six hour hold period was started. During this hold period, the reactor pressure increased from 70 psig to 105 psig from the generation of dimethyl ether. After the six hour hold was complete, the heaters were turned off and the vessel cooled. Once a safe (ambient) temperature was reached, the reactor slurry was dumped into a 5 gallon bucket, which was then placed overnight in a cold room to promote crystallization.

The crystallized product was then reslurried and filtered using a Whatman #1 filter paper. Due to the amount of material present, four separate funnel batches were required, with each cake washed with an amount of fresh methanol estimated to equal a 1:1 weight ratio of the cake. The wet cake was then placed back into the reactor with a sufficient amount of methanol to equal a 6:1 solvent ratio. The reactor was closed and purged three times with nitrogen to 100 psig. The vessel then was heated to 120° C. and held there for a 30 minute time period. After the 30 minute hold was complete, the heaters were turned off and the vessel cooled. Once a safe (ambient) temperature was reached, the reactor slurry was dumped into a 5 gallon bucket. As before, to promote crystallization, the bucket was then placed overnight in a cold room. The product was reslurried and filtered using a Whatman #1 filter paper as before, and the wet cake was placed in a vacuum oven set at 62° C. and dried.

The dried cake was loaded into a bottoms flask for distillation. Vacuum was pulled on the distillation column until a pressure of 20 torr was reached. The flask then was heated to a melt temperature of 238° C., the hot box surrounding the column was set at 204° C., and the filtered material was allowed to reflux for one hour. Thereafter, a splitter was started using a 2:1 reflux ratio. An initial cut was taken after 50 mls of overhead was collected. The balance of the overhead cuts was taken at 120 ml intervals.

After the run, the overhead cuts were allowed to cool overnight. Each cut was then ground and sampled. All cuts, except for the first, were blended into a batch sample. To increase the overall run yield, the first cuts from the first two distillation runs were added to the feed flask for the third distillation. This permitted us to discard only one first cut sample from the total of all three runs. At the end of the third distillation run, all three batch samples were made into a final composite.

Purity levels were calculated by adding up all known and unknown components other than the desired product and subtracting them from 100%. Purities were determined by liquid chromatography (99.87%), gas chromatography (99.95%) and nuclear magnetic resonance spectroscopy (99.72%). One impurity, by mass spectroscopy and consistent with NMR data, was 1-bromo-5-carbomethoxynaphthalene at a level of about 2,400 ppm. An acid number of 2 meq/kg was measured by titration. The only other known organic impurity identified was 2,6-NDC, which was identified by liquid chromatography (155 ppm), gas chromatography (9310 ppm) and nuclear magnetic resonance (205 ppm). Because the final product was distilled, inorganic analysis was done only for sulfur (non-detected) and bromine (6 ppm). Product color was excellent, $L^*=97.87$, $a^*=-0.26$, $b^*=1.56$.

The average organic purity of the recrystallized cake from three runs as described above was 99.61 wt % 1,5-NDC, 0.203 wt % 2,6-NDC and the balance treated as unknowns.

We have also purified 1,5-NDA using a process in which crude 1,5-NDA was reacted with sodium hydroxide, followed by carbon treatment and filtration, with subsequent acidification with hydrochloric acid. The product cake obtained from this process was slurried with fresh water, and filtered again from the resulting mother liquor. While relatively high yields (99+) of pure acid have been obtained, this process required high solvent and wash ratios and provided for relatively poor removal of sodium and chlorine, and is therefore not a preferred 1,5-NDA purification process.

1,5-NDC produced as discussed above, when polymerized with ethylene glycol to produce 1,5-PEN polymer, shows a higher amorphous density than 2,6-PEN. We believe this higher density is correlative to excellent barrier properties, which in turn means that 1,5-PEN may be a preferred material for use in certain packaging applications where good barrier properties are important to maintain the quality of the packaged material. Similarly, 1,5-NDA may be used in polymer applications as discussed below, in the same manner that 2,6-NDA's may be used analogously to 2,6-NDC's, as is known to those of ordinary skill in the polymer arts. The 1,5-naphthalenedicarboxyl polymer unit resulting generally from the use of either 1,5-NDA or 1,5-NDC will hereafter be referred to as a 1,5-naphthalenedicarboxyl moiety. Where that unit is part of a polyester, it will be referred to as a 1,5-naphthalenedicarboxylate moiety. Similarly, for example, the polymer unit resulting from a terephthalic acid in a polyester will be referred to as a terephthalate moiety.

Oligomerization of purified 1,5-NDC is described in Examples 2 and 3, below, and the preparation of a PET/1,5-NDC copolymer, is described in Example 4.

EXAMPLE 2

Ethylene glycol and 1,5-NDC was transesterified at a temperature of 180° C. and an ethylene glycol to 1,5-NDC molar ratio of about 1.6–2.2 without the use of a knock-back condenser. Although these conditions are expected to result in complete transesterification under commercial conditions in the presence of a knock-back condenser, complete transesterification did not occur in this Example, as confirmed by the presence of methyl groups in the reaction mixture by nuclear magnetic resonance analysis.

EXAMPLE 3

The reaction of Example 2 was performed at a temperature of 200–210° C. and at an ethylene glycol to 1,5-NDC molar ratio of 3.0 to 1.0. Oligomers were produced which had an inherent viscosity of 0.05 dL/g, and a 1.15/1.00 ethylene glycol to naphthalate ratio. The presence of methyl ester end groups as measured by nuclear magnetic resonance was about one percent. Such oligomers are believed to be consistent with most current commercial requirements. When solid-stated to an inherent viscosity of about 0.4 dL/g, we expect that the glass transition temperature of the 1,5-PEN will be about 87° C., with a melting temperature of about 235 to 240° C., and a rate of crystallization between that of PET and 2,6-PEN. These characteristics are in the range that makes the polymer particularly useful in packaging applications and for the fabrication of formed materials.

EXAMPLE 4

A PETN-8 copolymer, containing a ratio of 8 mole percent 1,5-NDC to 92 mole percent polyethyleneterephthalate (PET), was prepared by conducting an initial transesterification reaction at a temperature of 193° C. for a period of about 120 minutes, followed by a second transesterification step at 215° C. for a period of about 60 minutes. Subsequent polycondensation reaction of the copolymer for a period of 174 minutes at a temperature of 280° C. and an agitator turndown ratio of 50–60 rpm yielded a copolymer having an inherent viscosity of approximately 0.60 dL/g. When compared to a 2,6-NDC PETN-8 material prepared in a similar manner, the required polycondensation time was approximately 45% longer for the 1,5-NDC-based material.

Based on the above example, we believe that 1,5-NDA or 1,5-NDC may be used at low levels from about 1 to 10 mole percent in PET polymer compositions instead of, or in combination with 2,6-NDC, in polymers substantially comprised of polyethyleneterephthalate (such as in the PETN-8 example above), to improve the properties of the PET without substantially impacting the processability and cost of the polymer.

We also believe that compositions containing the 1,5-naphthalenedicarboxylate structural unit can be used to produce linear polyamides and copolyamides. These compositions can be used as fibers, films, shaped articles, hollow containers for packaging, engineering polymers, barrier packaging resins and other applications where the noted properties of the compositions are useful. These novel polyamides and copolyamide compositions are semicrystalline and absorb low levels of water, and unexpectedly have crystalline melting temperatures of less than 300° C.

Preferably, the homopolyamide compositions comprise 1,5-NDA and aliphatic or cycloaliphatic diamine moieties containing two to twenty carbon atoms. The acids in the copolyamide compositions comprise 1,5-NDA and up to 40 mole percent (of the total acid mole percent) of a second aliphatic or aromatic dicarboxylic acid, as well as an aliphatic or cycloaliphatic diamine containing two to twenty carbon atoms.

Examples of aliphatic dicarboxylic acids useful in these copolyamide compositions are $C_{3-20}$ dicarboxylic acids, especially adipic acid. Examples of aromatic dicarboxylic acids useful in these compositions are $C_{8-20}$ acids, especially terephthalic acid, isophthalic acid, and 2,6-NDA. The compositions also include 1,5-NDA when used with a diamine component which is a 1:99 to 99:1 mixture of two or more $C_{2-20}$ aliphatic or cycloaliphatic diamines.

The preparation of poly(hexamethylene-1,5-naphthalamide), polymer of the type discussed above, is described in detail in Example 5, below.

EXAMPLE 5

Poly(hexamethylene-1,5-naphthalamide) can be prepared in the following manner.

Add 648 g of 1,5-naphthalenedicarboxylic acid, 356 g of 1,6-hexamethylenediamine, 213 g of deionized water, and 0.5 g of sodium hypophosphite as catalyst, into a 4CV Helicone reactor (manufactured by Atlantic Research) which is pre-heated to 88–100° C. The temperature control is set for 320° C. and the agitator is set at 10 rpm. After about 26 minutes, the pressure in the reactor reaches 120 psi. Maintain the pressure at 120 psi for an additional 15 minutes, resulting in a melt temperature of 506° F.

Reduce the pressure to 100 psi over a 3 minute period and maintain the pressure at 100 psi for about 10 minutes. Thereafter, reduce the pressure to atmospheric pressure over 2 minutes. The melt temperature will be about 263° C. and an increase in the melt viscosity will be observed.

Remove the polymer from the reactor. The polyamide inherent viscosity value (measured in 60/40 phenol/tetrachloroethane at 30° C.) is 0.91 dL/g. The white polyamide is drawn into fibers.

Another novel use of 1,5-naphthalate-based material is in the manufacture of fibers. While 2,6-NDC has been used to produce fibers exhibiting excellent stiffness and chemical resistance, 2,6-NDC is difficult to use in typical fiber fabrication equipment. Because most fiber fabrication equipment is designed to be used with PET, which melts in the range of 250 to 255° C., use of 2,6-NDC, with its higher melting range of about 262–267° C., requires the use of upgraded extrusion equipment, such as the use of more powerful heating elements and longer barrels. Post-extrusion stretching of 2,6-NDC-containing fibers also is more difficult, as 2,6-PEN has a very high glass transition temperature of about 127° C. (compared to about 80° C. for PET), making use of conventional PET stretching equipment problematic.

1,5-PEN, on the other hand, exhibits a 235° C. melting temperature (lower than PET) and a glass transition temperature of about 85 to 87° C. (advantageously higher than PET), making the use of 1,5-PEN for fibers a preferred way to obtain the stiffness, chemical resistance, and UV barrier properties that PEN-containing fibers are known to exhibit.

The advantages in use of 1,5-naphthalate-based polymers over their 2,6-naphthalate counterparts are not limited to improved fiber processing as discussed above. The lower glass transition temperature and melting point are expected to provide for simpler manufacture of preforms, molded products and films generally. For example, the lower melting point can provide an advantage when molding thin wall parts or injection molding articles, where good material flow through narrow mold spaces is critical. Use of a 1,5-NDC-based material at its lower melting temperature will also decrease yellowing of polymer and decrease production of acetaldehyde byproduct. The lower Tg and melting point of 1,5-NDC also make it a substitute for comonomers such as isophthalic acid, which will provide for improved barrier properties relative to that comonomer.

These advantages similarly can be exploited in connection with the production of liquid crystal polymer materials. The typically high processing temperature of LCP materials using 2,6-NDC can be lowered by the use of 1,5-NDC.

We also believe that differences in the UV absorption characteristics of 1,5-NDC and 2,6-NDC may make the use of 1,5-NDC preferable in certain applications. The ultraviolet absorption maximum for 1,5-NDC is about 320 nanometers, while the absorption maximum for 2,6-NDC is about 380 nanometers. 1,5-NDC would therefore be preferred where protection in the deep ultraviolet range was desired. The difference in absorption maxima also could be advantageously exploited in a material containing both 1,5- and 2,6-NDC, either as comonomers or separate layers or components, where a wide range of UV resistance or protection was desired.

1,5-NDC also is believed to be more soluble in many organic solvents, such as styrene, than its 2,6-counterpart. This increased solubility can improve reactivity during polymerization and otherwise result in greater ease of use than would be attained from using 2,6-NDC.

The intermediates of 1,5-NDC production have other uses which can be exploited. For example, we believe that naphthalenic intermediates such as 5-orthotolylpentene, 1,5-dimethyltetralin, 1,5-dimethylnaphthalene, as well as 2,6-DMN produced during the manufacture 2,6-NDC, are useful as industrial solvents, heat transfer fluids, synthetic lubricants, and intermediates for agrichemicals and pharmaceuticals.

An example of the use of 5-OTP as a pharmaceutical intermediate is in the synthesis of drugs such as Abbott Laboratories ABT-839 anti-cancer drug. In this synthesis, a diene side chain can be added to 5-OTP by way of a dehydrogenation reaction, followed by reaction of the side chain with any of a number of electrophilic compounds in a Diels-Alder reaction to produce substituted biphenyl moieties of a type useful in the synthesis of drugs such as ABT-839. Use of 5-OTP as a starting material is believed to substantially reduce the number of synthesis steps otherwise required in producing such a drug.

1,6-dimethyl naphthalene has been used for a reactant in the preparation of octahydrobenzo-(f)-quinoline-based receptor agonists and antagonists, as disclosed in U.S. Pat. No. 5,863,928, and 1,5- and 2,6-naphthalenes may be useful in the synthesis of analogous compounds. 1,5-DMN has been used as a starting material in the preparation of the aldose reductase inhibitor Tolrestat as described in U.S. Pat. No. 4,562,286.

An example of the use of the intermediate 1,5-DMT in an application other than the synthesis of NDA's and NDC's would be its use as a substitute for other tetralins in synthesis schemes. For example, 1,5-DMT could be used as a substitute for tetralin in the reaction with styrene to produce heat transfer fluids such as the RP brand fluids available from Dow Chemical Company.

Dimethylnaphthalenes also are useful in printing and other graphic imaging applications. For example, sulfonated 1,5-naphthalene has been used in connection with the preparation of stable ink-jet inks as discussed in Japanese Patent No. 10298474, and 1,5-DMN has been used directly as a major (60%) component of ink-jet inks as disclosed in Japanese Patent No. 07138509. Sulfonated 2,6-naphthalene has been condensed with formalin to produce water-insoluble inks, such as disclosed in Japanese Patent No. 10298477, and 2,6-naphthalenes also are useful for increasing the sensitivity of laser radiation-induced thermal imaging systems, such as is disclosed in U.S. Pat. No. 5,747,217. 2,6-DMN also is useful as a starting point for the synthesis acryloldimethylnaphthalenes that can be used as photoresists, which are used, for example, in the preparation of printed wiring boards, as disclosed in Japanese Patent No. JP 09255726. We believe that 1,5-naphthalenes may be similarly useful in these and related graphics arts and imaging applications.

Agrichemical uses of dimethylnaphthalenes include the use of DMN's as a sprout inhibitor in the fogging of potato storage sheds, such as disclosed in patent application W.O. 94-US11419.

Dimethylnaphthalenes such as 1,5- and 2,6-DMN also are useful as starting materials for a wide variety of polymers, such as naphthalenenitriles, which can be produced by the catalytic reaction of DMN and ammonia in the presence of oxygen as disclosed in Japanese Patent Application No. 07126238, and the preparation of dibenzoyinaphthalene monomers of the type disclosed in Japanese Patent No. 06234848. They are also useful for producing other substituted naphthalenic systems such as 1,2,5,6-naphthalenetetracarboxylic acid as disclosed, for example, in Japanese Patent No. JP 05117202, or halogenated naphthalenes such as 2,6-bis (bromomethyl) naphthalene as disclosed in Japanese Patent No. 04282327.

Dimethylnaphthalenes also can be used as catalysts for the preparation of inorganic chemicals. For example, lithium aluminum hydride can be prepared by reacting lithium and hydrogen in the presence of a DMN catalyst as described in Chinese Patent Nos. 1033610 and 1011218.

Other industrial uses of dimethylnaphthalenes include the preparation of other substituted naphthalenic materials for impregnating electrical insulating materials such as the insulating paper used to prepare underwater cables as reported in U.S. Pat. No. 4,225,747, as materials for the synthesis of or for use as organoleptic agents, as, for example, discussed in U.S. Pat. No. 3,702,253; as reagents for making adhesives or as adhesive agents for bonding polystyrene or other organic materials, such as disclosed in Japanese Pat. No. 48102844; and as antibacterial agents in other organic systems, such as jet fuel, as disclosed in U.S. Pat. No. 3,361,545.

Other syntheses and end uses related to the foregoing synthesis of dimethyl-1,5-naphthalenedicarboxylate and its intermediates will be apparent to those skilled in the art based on the information provided herein. The scope of our invention, therefore, is intended to be limited only by the following claims.

We claim:

1. A process for manufacturing dimethyl-1,5-naphthalenedicarboxylate comprising the steps of:
   dehydrogenating 1,5-dimethyltetralin to produce 1,5-dimethylnaphthalene;
   oxidizing the 1,5-dimethylnaphthalene obtained from the dehydrogenating step to produce 1,5-naphthalenedicarboxylic acid without performing an intervening isomerization step; and thereafter
   esterifying the 1,5-naphthalenedicarboxylic acid obtained from the oxidizing step in the presence of methanol to produce dimethyl-1,5-naphthalenedicarboxylate.

2. The process of claim 1 further including the step of preparing the 1,5-dimethyltetralin by cyclizing 5-orthotolylpentene in the presence of an acid catalyst.

3. The process of claim 2 further including the step of preparing the 5-orthotolylpentene by reacting orthoxylene and butadiene.

4. The process of claim 1 wherein the dehydrogenation reaction is conducted in the presence of a supported noble metal catalyst at a temperature between about 150 and 250° C. and a pressure from about 0.3 to 5.0 atmospheres.

5. The process of claim 1 wherein the oxidizing step is a liquid phase oxidation conducted in the presence of a catalyst comprising cobalt, manganese and bromine in the presence of a solvent comprising a monocarboxylic acid.

6. The process of claim 1 wherein the esterifying step is conducted by heating a mixture of methanol and 1,5-naphthalenedicarboxylic acid to a temperature between about 80 and 200° C. at a pressure between about 3 and 15 atmospheres, and wherein the temperature and pressure are selected to maintain at least a portion of the methanol in a liquid phase.

7. The process of claim 1 further including recrystallizing 1,5-dimethylnaphthalene produced in the dehydrogenating step prior to performing the oxidizing step, wherein the recrystallizing step is performed by adding a melt comprising the 1,5-dimethylnaphthalene produced in the dehydrogenation step to a recrystallization solvent maintained at a temperature at least 60° C. less than the temperature of the added melt during the recrystallization step.

8. The process of claim 1 further including distilling the 1,5-dimethyltetralin to a purity of at least 95 weight percent prior to performing the dehydrogenating step.

9. The process of claim 1 in which the dehydrogenating step is performed in the presence of a catalyst comprising platinum and potassium on a zinc aluminate spinel support.

* * * * *